United States Patent
Yeung et al.

[11] Patent Number: 5,863,526
[45] Date of Patent: Jan. 26, 1999

[54] HOMOPOLYMERS PREPARED FROM AMMONIUM QUATERNARY SALTS OF AMINOALKYLACRYLAMIDES

[75] Inventors: Dominic Wai Kwing Yeung; Stan Lem, both of Ontario, Canada; Fred Robinson, Newtown, Pa.; Michael Prendergast, Jackson, N.J.

[73] Assignee: Rhone-Poulenc, Inc., Monmouth Junction, N.J.

[21] Appl. No.: 785,816

[22] Filed: Jan. 10, 1997

[51] Int. Cl.⁶ .......................... A61K 7/06; A61K 31/785; A61K 31/795
[52] U.S. Cl. ...................................... 424/70.11; 424/78.35
[58] Field of Search ................................ 424/70.11, 78.35

[56] References Cited

U.S. PATENT DOCUMENTS

| | | | |
|---|---|---|---|
| 3,910,862 | 10/1975 | Barabas et al. | |
| 3,986,825 | 10/1976 | Sokol. | |
| 4,075,183 | 2/1978 | Kawakami et al. | |
| 4,111,922 | 9/1978 | Berde et al. | 526/292 |
| 4,152,307 | 5/1979 | Shibahara et al. | |
| 4,180,643 | 12/1979 | Moss et al. | 528/52 |
| 4,419,344 | 12/1983 | Strasilla et al. | |
| 4,883,657 | 11/1989 | Williams et al. | 424/72 |
| 4,954,335 | 9/1990 | Janchipraponvej. | |
| 4,956,430 | 9/1990 | Tazi. | |
| 4,973,637 | 11/1990 | Morgan et al. | |
| 5,427,773 | 6/1995 | Chaudhuri et al. | |
| 5,476,650 | 12/1995 | Patel | 424/70.2 |
| 5,756,436 | 5/1998 | Royce et al. | 510/122 |

FOREIGN PATENT DOCUMENTS

| | | | |
|---|---|---|---|
| 2137901 | 6/1995 | Canada. | |
| 0 047 714 A2 | 3/1982 | European Pat. Off. | C08L 33/14 |
| EP 0 275 153 A2 | 7/1988 | European Pat. Off. | A61K 7/06 |
| 2 511 232 | 2/1983 | France | A45D 7/04 |
| WO 89/07435 | 8/1989 | WIPO | A61K 7/00 |
| WO 97/26860 | 7/1997 | WIPO | A61K 7/50 |
| WO 97/29736 | 8/1997 | WIPO | A61K 7/50 |
| WO 97/35543 | 10/1997 | WIPO | A61K 7/06 |

OTHER PUBLICATIONS

Description of Polycare 133, 1990 "Polymethacrylamidopropyl Trimonium Chloride."

*Primary Examiner*—Jeffrey Smith
*Assistant Examiner*—Wu C. Cheng
*Attorney, Agent, or Firm*—Scully, Scott, Murphy & Presser

[57] ABSTRACT

The present invention is directed to a hair conditioning composition comprising as the active ingredient, a homopolymer of the formula.

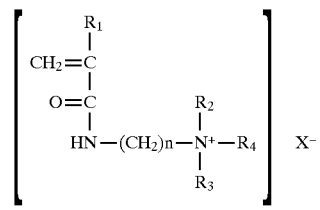

wherein $R_1$ is hydrogen or methyl;

$R_2$ and $R_3$ are independently lower alkyl;

$R_4$ is $C_2$–$C_{25}$ alkyl or aryl group;

n is 1–6; and

X is lower alkyl sulfate or aryl sulfonate and to the use thereof for treating hair.

31 Claims, No Drawings

HOMOPOLYMERS PREPARED FROM AMMONIUM QUATERNARY SALTS OF AMINOALKYLACRYLAMIDES

BACKGROUND OF THE INVENTION

1. Field of the Invention

The present application is directed to homopolymers prepared from ammonium quaternary salts of amino alkylacrylamides, the processes for preparing same, formulations containing these homopolymers and the use thereof in personal care formulations.

2. Description of the Prior Art

Polyquaternary polymers have been used in a variety of industrial formulations, including cosmetic formulations. However, to date, one of the most important applications is their use in hair and skin formulations, including hair shampoos and hair conditioning products. More specifically, they have been used to sufficiently condition the hair so that it holds a preset configuration.

Hair shampoos generally are formulated with highly effective synthetic surfactants, such as anionic surfactants, that clean the hair. The anionic surfactants not only remove the dirt and soil from the hair but concomitant therewith, they unfortunately also remove all of the sebum naturally present on the surface of hair fibers. As a result, shampoo compositions containing these surfactants leave the hair with an undesirable harsh, dull and dry touch or feel, usually called "creak", after the hair is shampooed and then rinsed with water.

Furthermore, thoroughly cleansed hair also is extremely difficult to comb, in either the wet or the dry state, because the individual hair fibers tend to snarl, kink and interlock with each other. If the hair is incompletely dried, such as hair dried with a towel, the hair has poor brushing properties, and after complete drying, the hair does not set well. The combing or brushing property of the hair remains poor and in low humidity atmospheres, the hair has undesirable electrostatic properties, causing the hair to "fly away", thereby reducing the brushing properties of the hair. The unsatisfactory combing or brushing property of hair immediately after shampooing also causes hair damage, such as split ends or hair breakage. In addition, shampooing of hair reduces the natural luster and resiliency of the hair, thereby giving the hair a dull appearance.

Thus, shampoos usually neither aid in the detangling of wet hair nor impart any residual conditioning benefits to dry hair, such as manageability or styleability of hair sets. The overall unsatisfactory condition of the shampooed hair necessitates the use of a conditioning composition to improve these undesirable physical characteristics. The conditioning composition may be applied separately from the hair shampoo as a post-shampoo treatment of the hair or may be incorporated into the hair shampoo. However, because many of the most widely used products for treating hair contain anionic surfactants and as explained hereinbelow, conditioning compositions usually contain cationic polymers as the active ingredient, and because cationic material are usually inactivated by reaction with anionic surfactants, it is customary to employ conditioner containing cationic materials as a separate composition, such as post-shampoo rinse, separately applied.

The conditioning agents that have been utilized in the prior art are cationic compounds such as cationic surfactants and cationic polymers. They render the hair more manageable. For example, the wet combing problem discussed hereinabove is solved by the use of these conditioners which coat the hair shaft and cause the individual hair shafts in a tress to resist tangling and matting because of the conditioner residue retained on the shaft. The ability of these cationic compounds to absorb or react with the keratinous material of the hair makes them the most desirable compounds for imparting the desired improvement in wet hair detangling and dry hair manageability. Many of these cationic compounds are polyquarternary polymers prepared from monomers with an ester functionality, for example, acrylate or methacrylate types, as a comonomer.

Although they are useful, these polyquaternary polymers containing esters have several disadvantages associated therewith. For example, they tend to be hydrolytically unstable to the extent that the formulation must avoid conditions conducive to hydrolysis during formulation, such as acidic or basic conditions and higher temperatures such as temperatures greater than about 30° C. Under these conditions, they decompose and catalytically hydrolyze as a result of contact with water, including trace amounts thereof, into the (meth) acrylic acid and the corresponding dialkylalkanolamine, resulting in significant lowering of viscosity and concomitant reduction in beneficial properties.

Moreover, the esters used heretofore lack hydrogen bonding capability with skin protein or hair keratin; consequently the hair substantivity, when applied, is not satisfactory.

Furthermore, commercial formulations used heretofore are indiscriminate in the anion utilized. For example, many hair care products utilize anions derived from organic and inorganic acids, such as hydrochloric acid, sulfuric acid, phosphoric acid, hydrobromic acid, hydroiodic acid, acetic acid, propionic acid, formic acid and the like. In the prior art conditioners, the preferred acid is hydrochloric acid, with the anion being a chloride ion. See, e.g., U.S. Pat. No. 4,973,637. However, the presence of a chloride is undesirable, especially because it is a skin irritant. In addition, many conditioning agents are adapted for use as a spray from a container. However, chlorides have corrosive properties, and over a period of time, results in the corrosion of the spray container.

Another problem associated with conditioners heretofore, especially those that absorb particularly strongly to the hair, is that they reduce the elasticity, body and set of the dried hair.

The need for improved compositions that condition the hair has long been recognized in the art. Therefore, although conditioning compositions for applications to freshly shampooed hair are well known, new and improved conditioning formulations based on cationic compounds are continually sought. These new conditioning compositions must overcome the problems discussed hereinabove. They must also be aesthetically acceptable to consumers, improve the wet combing and dry combing properties of hair, leave the dry hair with satisfactory cosmetic and physical properties, including, in particular, dry combing and feel, less hair coating, manageability, and body. The conditioners sought must be substantive to hair.

The present inventors have found a homogenous and clear cationic polymer which, when formulated into a hair conditioning composition, does not suffer from the disadvantages enumerated hereinabove. The resulting formulation is an excellent hair conditioner which gives the hair body moisture, combability, etc. Such formulations are not corrosive or skin-irritants, but yet are stable to pH changes and impart improved physical and cosmetic properties to the hair.

SUMMARY OF THE PRESENT INVENTION

Accordingly, the present invention is directed to a hair conditioning composition comprising as the active ingredient a homopolymer prepared by polymerizing a monomer of the formula:

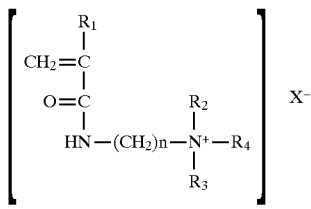    I wherein
$R_1$ is hydrogen or methyl;
$R_2$ and $R_3$ are independently lower alkyl or lower alkenyl;
$R_4$ is $C_1$–$C_{25}$ alkyl or aryl group;
n is 1–6 and
X is lower alkyl sulfate or aryl sulfonate.

It is also directed to a hair conditioning product containing said homopolymer. The present invention is also directed to a method of treating the hair, whereby the hair is conditioned by contacting the hair with a composition containing said homopolymer.

DETAILED DESCRIPTION OF THE INVENTION

The present compositions of the present invention finds wide application in formulations to provide hair conditioning properties, and viscosity building characteristics and to impart resistance to hydrolysis in acidic and alkaline solutions. They have excellent hair substantivity so that their conditioning effects endure for extended periods. As used herein, the term "conditioning" is intended to include the functions that enhance the feel and appearance of hair, including, inter alia, moisturizing, softening, lustering, and body building, of the hair.

As defined herein, unless indicated to the contrary, the term "lower alkyl" when used alone or in combination, refers to an alkyl group containing 1–6 carbon atoms. The alkyl group may be straight chained or branched. Examples include methyl, ethyl, n-propyl isopropyl, n-butyl, isobutyl, sec-butyl, t-butyl, n-pentyl, isopentyl, neopentyl, n-hexyl, and the like. The preferred alkyl group contains 1–5 carbon atoms, and the more preferred alkyl group contain 1–3 carbon atoms. Methyl is the preferred "lower alkyl" group.

As used herein, the term "aryl" when used alone or in combination, is an aromatic group containing only carbon ring atoms and containing 6–10 carbon ring atoms and up to a total of 15 carbon atoms. It also includes alkyl substituted aryl groups. Examples of aryl include phenyl, α- or β-naphthyl, tolyl, xylyl, and the like. The preferred aryl groups are phenyl and tolyl.

In Formula I, $R_1$ is defined as hydrogen or $CH_3$. When $R_1$ is $CH_3$, the homopolymer is derived from a methacrylamide derivative. It is preferred that $R_1$ is $CH_3$.

$R_2$ and $R_3$, as defined hereinabove, are independently preferably $C_1$–$C_5$ alkyl. It is preferred that $R_2$ and $R_3$ are the same. The most preferred alkyl is $C_1$–$C_3$ alkyl, including ethyl, and especially methyl. It is most preferred that $R_3$ and $R_2$ are the same and are both alkyl, e.g., ethyl and especially methyl.

The preferred $R_4$ groups are lower alkyl, especially $C_1$–$C_5$alkyl, and aryl. The preferred alkyl group contain 1–3 carbon atoms. They are preferably methyl and ethyl. It is also preferred that when $R_2$ and $R_3$ are alkyl, that $R_2$, $R_3$ and $R_4$ are the same.

The preferred values of n are 1–4, with 3 being the most preferred value.

The anion X is preferably $C_1$–$C_3$ alkyl sulfate or aryl sulfonate. The most preferred aryl sulfonate is p-toluene sulfonate.

The homopolymers of the present invention are prepared by subjecting the monomer of Formula I to polymerization, and especially free radical polymerization. The reaction is conducted in an oxygen-free environment, such as in the presence of an inert gas (e.g., helium, argon and the like), or nitrogen. The polymerization is carried out in an inert solvent, preferably lower alcohols and most preferably water.

Polymerization is initiated by adding a polymerization initiator. The initiators utilized are the usual free radical polymer initiators. Examples include organic peresters (e.g., t-butyl peroxypivalate, t-amyl peroxypivalate, t-butyl peroxy-α-ethylhexanoate, and the like); organic azo compounds (e.g. azobisamidinopropanehydrochloride, azobisisobutyronitrile, azobis-2,4-dimethylvaleronitrile, and the like); inorganic and organic peroxides, (e.g., hydrogen peroxide, benzyl peroxide, and butyl peroxide and the like), and oxidizing agents, such as persulfates (such as ammonium or alkali metal persulfate, and the like), chlorates and bromates (including inorganic or organic chlorates and/or bromates), the sodium salt of ethylene diamine tetraacetic acid (EDTA), reducing agents, such as sulfites and bisulfites (including inorganic and/or organic sulfites or bisulfites) oxalic acid, and ascorbic acid, and combinations thereof. The preferred initiators are water soluble. The most preferred initiators are sodium persulfate and azobisamidinopropanehydrochloride. Alternatively, initiation of polymerization can be instituted by irradiation with ultra-violet light. The amount of initiator utilized is in general a sufficient amount to effect initiation of polymerization. Preferably they are present in amounts ranging from about 0.001 to about 10% by weight of monomer and more preferably less than about 0.5% by weight based on the total weight of the monomer, and most preferably from about 0.005 to about 0.5% by weight based upon the weight of the monomer. The initiator is added in the polymerization either continuously or in incremental additions. The continuous or incremental addition of the initiator promotes the polymerization reaction. It is also essential to insure high molecular weight polymer. It has been found that repeated contact of unreacted monomers with fresh initiator, particularly during the final stages of reaction when monomer concentration is greatly reduced, drives the reaction to completion. The gradual or incremental addition also promotes more efficient and conservative use of initiator while permitting a shorter overall reaction time.

The polymerization is conducted under reaction conditions effective to polymerize the monomer of Formula I under an oxygen free atmosphere. Preferably, the reaction is conducted at a temperature ranging from about 30° C. to about 100° C. and more preferably from about 60° C. to about 90° C. The oxygen free atmosphere is maintained for the duration of the reaction, for example, the nitrogen purging is maintained throughout the reaction. The continuous purging of the reaction by constant ebullition of inert gas maintains the oxygen free atmosphere.

The quaternized monomer of Formula I is prepared by reacting an amino alkyl (meth)acrylamide of the formula

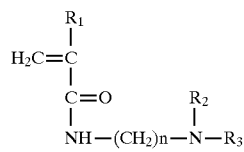

with sufficient amounts of quaternizing agent $(X(R_4)_2)$ to form the compound of Formula I under conditions effective for said quaternization. Preferred quaternizing agents include dialkyl sulfate, such as dimethyl sulfate, diethyl sulfate, and sulfonates, e.g., dodecyl p-toluene sulfonate, and the like. The reaction is preferably conducted in an inert solvent such as water, and the reaction is conducted at temperatures ranging from about room temperature to about 120° C.

Alternatively, the homopolymer can be prepared by first polymerizing a compound of Formula II in the presence of a free radical initiator under the free radical polymerization conditions described hereinabove followed by quarternizing the product therefrom under the quaternary reaction conditions described hereinabove. It is preferred that the polymerization is conducted on the quaternized product. Owing to this procedure, the homopolymer has substantially better reproducibility with regard to color, odor, molecular weight and viscosity, and in addition, the color, clarity of the polymer solution and odor are substantially improved. By using the quaternized dialkylaminoalkyl meth(acrylate) for the polymerization, the auto-catalytic hydrolysis of the dialkylaminoalkyl(meth)acrylate is suppressed, and it is thus possible to prepare the homopolymers having substantially greater product consistency and improved color and odor while, surprisingly, also exhibiting an extremely low residual monomer content.

The desired molecular weight of the polymer is attained by varying polymerization conditions in ways known to the skilled artisan, such as varying polymerization temperature (with the lower temperatures being conducive to the formation of high molecular weight polymers), monomer concentration, amount of initiator, and the like. However, the molecular weight of the polymerized product can be regulated by adding regulators such as isopropyl alcohol.

The homopolymer is also quite viscous, having a Brookfield viscosity (LVT, #3, 6 rpm, 25° C.) of at least about 7500 cps, at about 40% solids. In fact, the viscosity under these conditions preferably ranges to at least 100,000 cps or more, but it is more preferred that the viscosity range from about 7500 cps to about 20,000 cps at about 40% solids.

The intrinsic viscosity thereof ranges from about 0.5 to about 1.5 when measured in a 1N $NaNO_3$ solution at 30° C. Intrinsic viscosity is directly related to the molecular weight of the homopolymer, as described by the Mark Houwink Equation:

Intrinsic Viscosity=$KMW^{-\alpha}$ wherein
K is a constant for a specific polymer;
$\alpha$ is a different constant for a specific polymer; and
MW is the molecular weight.

It is preferred that the intrinsic viscosity of the homopolymer in 1N $NaNO_3$ solution measured at 30° C. ranges from about 0.7 to about 0.9.

It is critical to the product of the present process that it maintains the anion of the quaternizing agent utilized in the present process, and that it is not removed or replaced. It is the presence of the alkyl sulfate and/or the aryl sulfonates that permits the product to be non-corrosive and non-irritating to the skin or hair.

It has been found that the homopolymer of the present invention is more soluble in aqueous solutions relative to other commercial cations utilized in hair conditioning compositions.

The homopolymer produced by the process described hereunder is formulated into a hair conditioning composition. It is the active conditioning ingredient in the formulation and is present in hair conditioning effective amounts. The product is preferably present in an amount ranging from about 0.5% to about 5% by weight of the composition. Preferably, the product is present in an amount ranging from about 1% to about 4% by weight of the composition, and more preferably from about 1% to about 2.5% by weight of the composition.

In hair conditioning formulations the homopolymer produced by the present process is present in the hair condition composition in association with a cosmetic vehicle. The vehicle of the present composition is predominantly water, but organic solvents also can be included in order to facilitate manufacturing of the composition or to provide esthetic properties to the compositions, such as viscosity control. Suitable solvents include the lower alcohols, like ethyl alcohol and isopropyl alcohol; glycol ethers, like 2-butoxyethanol: ethylene glycol monoethyl ether; propylene glycol and diethylene glycol monoethyl ether or monomethyl ether, and mixtures thereof. These non-aqueous solvents can be present in the clear hair conditioning composition of the present invention in an amount from about 1 to about 50% by weight and in particular from about 5% to about 25% by weight relative to the total weight of the composition.

The compositions of the present invention are clear relatively viscous compositions that are stable to phase separation at a temperature of about 25° C. for an indefinite period of time.

The pH of the composition of the present invention ranges from about 3.5 to about 8.0 and more preferably from about 5 to about 7.5.

The composition of the present invention optionally contains additional ingredients. For example, the conditioning composition may be formulated into a hair shampoo product, and then is associated with nonionic, anionic, amphoteric and zwitterionic surfactants, well known in the art. Examples of anionic surfactants include sulfates such as alkyl sulfate, preferably containing 10–20 carbon atoms, (e.g., lauryl sulfate), alkyl ether sulfate, preferably containing 10–40 carbon atoms (e.g., lauryl ether sulfate), alkylamide sulfates preferably containing 10–20 carbon atoms, alkyl arylpolyether sulfate preferably containing 10–20 carbon atoms, monoglyceride sulfates; sulfonates, e.g. alkyl sulfonate, preferably containing 10–20 carbon atoms, alkylamide sulfonates, preferably containing 10–20 carbon atoms, alkylaryl sulfonates preferably containing 10–40 carbon atoms and α-olefin sulfonates, preferably containing 10–20 carbon atoms; sulfosuccinic acid derivatives, e.g., alkyl ($C_{10}$–$C_{20}$) sulfosuccinates, alkyl ($C_{10}$–$C_{20}$) ether sulfosuccinates, alkyl ($C_{10}$–$C_{20}$) amide sulfosuccinates, and alkyl ($C_{10}$–$C_{20}$) amide polyether-sulfosuccinates; sarcosinates, e.g., ($C_8$–$C_{22}$) alkyl or ($C_8$–$C_{22}$)alkenyl sarcosinates; phosphate surfactants, e.g., alkyl ($C_{10}$–$C_{20}$) phosphates, or alkyl ($C_{10}$–$C_{20}$) ether phosphates, and the like. Examples of these ionic surfactants are described in U.S. Pat. No. 4,419,344 to Strasella, et al., the contents of which are incorporated by reference. If present, these ionic surfactants are preferably present in amounts ranging from about 0.1% to 5% by weight and more preferably from about 0.1% to 2% by weight.

Examples of nonionic surfactants include fatty acid alkanolamides, e.g., mono or diethanolamine adduct (lauric diethanolamide, coconut diethanolamide), amine oxides, and ethoxylated nonionics, e.g., ethoxylated forms of alkylphenols, fatty alcohols, fatty esters, and mono and diglycerides, and the like; these examples all contain preferably 10–22 carbon atoms. These are described in Kirk-Othmer, Encyclopedia of Chemical Technology, Vol. 12, p. 887, John Wiley and Sons, Inc. 1994 and U.S. Pat. No. 4,954,335 to Janchipraponvej; the contents of which are incorporated by reference. They are present in amounts ranging from 0.1% to about 5% by weight and more preferably from about 0.1 to about 2% by weight.

The amphoteric surfactants, also known as ampholytics, are both positively and negatively charged, and are usually derivatives of imidazolines or betaines, such as oleamidopropylbetaine and the like. They may also be associated with the homopolymer of the present invention in the hair conditioning compositions of the present invention. Sodium lauroamphoacetate may also be utilized in non-stinging shampoos. They are present in amounts ranging from about 0.1% to about 5% by weight and more preferably from about 0.1% to about 2% by weight.

Another optional ingredient in the composition includes a polyhydric compound. The polyhydric compound is present especially when the composition contains surfactants for it helps couple the homopolymers and the surfactant to provide a clear non-turbid aqueous-based hair conditioning composition. The polyhydric compound can be a glycol, a triol or polyol. Specific examples include, but are not limited to ethylene glycol, propylene glycol, butylene glycol, hexylene glycol, diethylene glycol, triethylene glycol, dipropylene glycol, tripropylene glycol, glycerol or polyethylene or polypropylene glycol having an average molecular weight up to about 500. If present, it is present in amounts ranging from about 1% to about 20% by weight of the composition.

In addition, additives may also be optionally added to the compositions of the present invention, such as fragrances, dyes, hair colorants, dandruff control agents, hydrotropes, foam stabilizers, preservatives, (e.g., methyl and propyl parabens, DMDM hydantoin, diazolidinyl urea, imidazolidinyl urea, and the like), water softening agents, acids, bases, buffers and the like. These optional additives if present usually will be present in weight percentages of less than about 2% each, or from about 5% to about 10% by weight of the composition in total.

The clean hair conditioning compositions of the present invention also may optionally include thickeners that are generally used in this art. Example includes sodium alginate, guar gum; xanthan gum; gum arabic, cellulose derivatives, such as methylcellulose, hydroxyethyl cellulose, hydroxypropyl methyl cellulose, and carboxymethylcellulose; and various polymeric thickeners, such as carboxyvinyl polymers, e.g., polyacrylic acid derivatives, and polyvinylalcohols and the like. These thickeners if present, are present in an amount ranging from about 0.1% to about 3%, and preferably from about 0.25% to about 1% by weight relative to the total weight of the composition.

Other optional materials include inorganic salts (e.g., alkali halides, sulfates or acetates, such as sodium, potassium, lithium, ammonium chloride, bromides, sulfates or acetates), humectants and similar material to provide esthetic properties and desirable physical properties to the composition. Preferably, such optional materials, if present, are present in weight percentages ranging from about 0.1% to about 10% each and from about 0.1% to about 20% in total, relative to the total weight, of the composition.

The composition of the present invention may be formulated into a solution, cream, spray, lotion or mousse, in accordance with procedures known to the skilled artisan. For example, if made into a spray, the composition is introduced to a suitable aerosol container; it is then pressurized with propellents.

As indicated hereinabove, the cationic homopolymer prepared by the present invention has a greater solubility in aqueous solutions than other cationic homopolymers used in hair conditioning compositions. As a result, the hair conditioning composition of the present invention is easier to prepare. Without wishing to bound, it is believed that the increased solubility facilitates the mixing of the various components, especially in a water carrier.

In addition, as a result of the increased solubility of the homopolymer in water, it is easier to remove the hair conditioning composition from the hair after application thereof by rinsing with water.

The composition of the present invention imparts exceptional hair conditioning properties to treated hair. It has curl retention capability. It can be used to treat untangled as well as tangled hair. It is also consumer appealing. The product is clear and maintains product stability over long storage times. The clear composition of the present invention coats the hair very effectively and also is especially easy to rinse from the hair.

In addition, the hair conditioning composition of the invention also provides the further benefits of not leaving the hair flacky or sticky; not forming a crust and thereby providing combability and providing manageable and styleable hair having body. In addition, after treating the hair with the composition of the present invention, the hair has a soft, silky natural feel, has body, and is shiny, thickened, manageable and combable.

Other properties provided by the present composition is that when applied to the hair, the hair maintains a firm but flexible hold and has curl retention. Furthermore, it softens permed and treated hair. In addition, it has a pH stability over a broad range.

Thus, the easy to apply, clear composition of the present invention provide excellent wet comb and excellent dry comb properties to the hair, and the hair demonstrates improved and physical and cosmetic properties such as gloss, thickness, softness, manageability, body and less coating. In short, the treated hair has an enhanced sensitivity imparted thereto.

The following non-limiting examples further illustrate the invention.

Unless indicated to the contrary, all percentages and parts are by weight.

EXAMPLE 1

Preparation of Quaternary Monomer of Dimethylaminopropyl Methacrylamide and Dimethylsulfate To a 5 liter reaction flask, demineralized water (900.0 g), and dimethylamino propyl methacrylamide (DMAPMA) (2107.7 g) were added. While maintaining the temperature below 35° C., the mixture was purged with a slow stream of air and dimethylsulfate (DMS) (1514.4 g) was added to the mixture. The reaction mixture was held at 30° C. for two hours following the complete addition of DMS. The pH of the resulting solution of the quaternary monomer was then adjusted to about pH 7 with concentrated sulfuric acid (18.3 g). The concentration of the resulting monomer was about 80% (w/w), and the viscosity was about 90 cps.

EXAMPLE 2

Preparation of Quaternary Monomer of Dimethylaminopropylmethacrylamide and Dimethylsulfate The above quaternary monomer was prepared from DMAPMA (534.7 g) and diethylsulfate (DES) (460 g) using the procedure of Example 1. The concentration of the resulting monomer was about 80% (w/w) and the viscosity was about 80 cps.

EXAMPLE 3

Preparation of Quaternary Monomer of Dimethylamino Propylacrylamide with Dimethyl Sulfate The above-identified quaternary monomer was prepared from dimethylaminopropylacrylamide (DMAPA) (410.5 g) and dimethylsulfate (313.0 g) utilizing the procedure of Example 1. The concentration of the monomer in the product was about 80%, and the viscosity was about 90 cps.

The results of Experiments 1–3 are tabulated hereinbelow in Table 1.

TABLE I

PREPARATION OF QUATERNARY MONOMERS

| MON-OMER | Aminoalkyl (Meth) Acrylamide | Quaternarizing Agent | Appearance | Viscosity | pH | Solids |
|---|---|---|---|---|---|---|
| I | DMAPMA | DMS | Clear | 90 cps | 7.3 | 80% |
| II | DMAPMA | DES | Clear | 80 cps | 6.6 | 80% |
| III | DMAPA | DMS | Clear | 80 cps | 6.9 | 80% |

EXAMPLE 4

Homopolymerization of DMAPMA and DMS

Into a 3-liter reaction flask were added the quaternary monomer of Example 1 (66.3 g), demineralized water (875.0 g) and Versene 100®, i.e., the sodium salt of EDTA (0.66 g). The mixture was then heated under slow nitrogen purging to 75° C.

The quaternary monomer solution thus prepared (80%, 1283.7 g) was metered separately but simultaneously into the reaction vessel with initiator Wako V-50 (azobisamidinopropanehydrochloride) solution (0.99 g in 473.4 g demineralized water). The addition time for the monomer solution was 150 minutes, while it was 180 minutes for the initiator solution. The temperature was maintained at 75° C. for 30 minutes following the completion of the additions, then the mixture was heated to 90° C. Another portion of Wako V-50 initiator (0.27 g in 1.35 g demineralized water) was added to the resulting mixture all at once and the reaction temperature was maintained at 90° C. for 60 minutes. After 60 minutes at 90° C., a third portion of Wako V-50 initiator (10.55 g in 1.35 g demineralized water) was added and maintained at 90° C. for another 60 minutes. The resulting polymer solution was clear and viscous.

This procedure was repeated several times and the results are tabulated in Table 2.

EXAMPLE 5

Homopolymerization of the Product of DMAPMA and DES

The above product was prepared utilizing the procedure of Example 4 except that the quaternary monomer resulting from DMAPMA and DES was utilized. The results are tabulated in Table 2.

EXAMPLE 6

Homopolymerization of the Product of DMAPA+ DMS

The above product was prepared utilizing the procedure of Example 4, except that the quaternary monomer resulting from DMADA and DMS was utilized. The results are tabulated in Table 2.

TABLE 2

RESULTS HOMOPOLYMERS

| Example | Monomer | Initiator | Polymerization Temperature | Solids % | Viscosity | pH |
|---|---|---|---|---|---|---|
| 4a | I | Wako V-50, 0.092% | 75 C. | 40.0 | 10,000 cps. | 6.6 |
| 4b | I | Wako V-50, 0.092% | 75 C. | 39.4 | 10,400 cps. | 6.5 |
| 4c | I | Wako V-50, 0.092% | 75 C. | 39.9 | 10,800 cps. | 6.5 |
| 4d | I | Wako V-50, 0.092% | 75 C. | 39.6 | 14,600 cps. | 5.5 |
| 4e | I | Wako V-50, 0.092% | 75 C. | 40.1 | 11,000 cps. | 6.2 |
| 4f | I | Wako V-50, 0.092% | 75 C. | 40.3 | 10,700 cps. | 6.2 |
| 4g | I | Wako V-50, 0.092% | 75 C. | 40.3 | 11,200 cps. | 6.4 |
| 4h | I | Wako V-50, 0.092% | 75 C. | 40.1 | 11,600 cps. | 6.8 |
| 4i | I | Wako V-50, 0.092% | 75 C. | 40.0 | 11,800 cps. | 3.9 |
| 4j | I | Wako V-50, 0.092% | 75 C. | 40.0 | 12,000 cps. | 3.8 |
| 4k | I | Wako V-50, 0.092% | 75 C. | 39.9 | 14,800 cps. | 4.0 |
| 4l | I | Wako V-50, 0.092% | 75 C. | 39.9 | 14,200 cps. | 4.1 |
| 5 | II | Wako V-50, 0.122% | 75 C. | 40.0 | 12,400 cps. | 6.8 |
| 6a | III | Wako V-50, 0.046% | 75 C. | 40.0 | 7,800 cps. | 5.0 |
| 6b | III | Wako V-50, 0.092% | 65 C. | 40.0 | 83,000 cps. | 5.0 |

EXAMPLE 7

A shampoo formulation was prepared from the following ingredients, which are indicated in parts by weight

| | |
|---|---|
| Sodium Lauryl Ether Sulfate | 50.0 |
| Sodium chloride | 4.0 |
| Coconut Diethanolamide | 10.0 |

-continued

| | |
|---|---|
| Poly Ethylene Glycol 6000 Distearate | 2.0 |
| Oleamidopropyl Betaine | 30.0 |
| Sodium Lauryl Sulfate | 96.0 |
| DMDM Hydantoin | 0.6 |
| Distilled Water | 6.0 |
| Homopolymer of Example 4a | 1.0 |

The resulting formulation was clear and showed excellent compatibility of the quaternary homopolymer with the formulation. The viscosity of the formulation was about 3200 cps and had a pH of about 7.2.

The Shampoo Formulations utilizing the other homopolymers of Example 4 are also prepared.

EXAMPLE 8

A shampoo formulation is prepared as in Example 7 except that the homopolymer of Example 5 was utilized.

EXAMPLE 9

Two shampoo formulations are prepared as in Example 8 each one containing one of the homopolymers product of Example 6.

EXAMPLE 10

A shampoo formulation is prepared as in Example 8, except that the homopolymer of Example 7 was utilized.

EXAMPLE 11

A styling mousse formula is prepared from the following ingredients:

| | % by Weight |
|---|---|
| MIRATAINE BET 0-30 ® | 1.5 |
| MIRATAINE CBC ® | 1.5 |
| A Homopolymer of Example 4 | 2.0 |
| Fragrance, Dye, preservative | 0.5 |
| Water | 95.0 |

The MIRATAINE BET 0-30® (oleamidopropyl betaine) and MIRATAINE CBC® (cocoamidopropyl betaine) are slowly blended with water in a mixing vessel until uniform. With smooth agitation, a homopolymer of Example 4 is blended in and mixed until uniform. Finally, compatible fragrance, dye and preservatives are added.

EXAMPLE 12

A moisturizing styling spray is prepared as follows:

| | % by Weight |
|---|---|
| SD Alcohol 40 | 15.0 |
| Propylene Glycol. | 0.50 |
| Homopolymer of Ex. 4 | 2.00 |
| Water | 82.50 |
| Fragrance Dye and Preservative | 0.50 |

Propylene glycol is mixed with water with rapid but smooth agitation. One of the homopolymers of Ex. 4 is slowly blended in, and slowly mixed until completely uniform. The SD Alcohol 40 is then added followed by the addition of fragrance, dye and preservatives, and the resulting product is mixed until uniform.

The following experiments relate to various tests that were conducted on the formulation prepared in Example 4a.

EXAMPLE 13

Wet Comb Evaluation 1 mL of 0.5% aqueous solution of the polymer prepared in Example 4a was added (0.5% solids) to the wet tress, European brown hair which was oxidatively damaged. The tress was massaged for one minute. After a 1–2 minute standing period, the hair was rinsed for 30 seconds. The testing involved the use of a Dia-Stron stress tester which measures combing force. The force was calculated by use of Dia-Stron software in combination with multiple combing cycles. Eight combings per tress were used before and after treatment with the polymer. As a standard, hair tresses which were identically processed, except for the addition of the conditioning agent, were used. Lower values for work and peak loads as compared to the untreated samples are considered desirable.

The results are given in the following Tables.

TABLE 3

| | TOTAL WORK LOAD (Kg of combing force) | | |
|---|---|---|---|
| TRESS ID | UNTREATED | TREATED | % REDUCTION |
| A | 0.186 | 0.122 | 34.41 |
| B | 0.202 | 0.112 | 44.55 |
| C | 0.228 | 0.119 | 47.81 |

AVG % WORK LOAD REDUCTION: 42.26

TABLE 4

| | TOTAL PEAK LOAD (grams of combing force) | | |
|---|---|---|---|
| TRESS ID | UNTREATED | TREATED | % REDUCTION |
| A | 268 | 150 | 44.03 |
| B | 307 | 146 | 52.44 |
| C | 306 | 144 | 52.94 |

AVG % PEAK LOAD REDUCTION: 49.80%

The product in 0.5% aqueous solution (w/w) showed excellent work load reduction of untreated damaged. In addition, the product exhibited excellent peak load reduction indicating excellent conditioning of tangled hair.

EXAMPLE 14

The next set of experiments tested the curl retention of the polymer prepared in Example 4a.

The tresses were prepared as follows: 1 mL of the polymer prepared in Example 4a (4.0% solids) was applied to the wet tress with no rinse and massaged into the tress for one minute. The tress was curled onto a 1 inch roller and then placed in oven at 45° C. for 2 hours. At the conclusion of the two hours, the curled tress was allowed to stand at room temperature for 16 hours and placed in a humidity chamber thereafter. The tress was carefully removed from the roller and immediately suspended vertically from a holding fixture. The length of the tress was recorded. The test conditions were 25° C./90% RH. The % curl retention was determined by the length of the hair at different time levels of exposure. Constant values for retention over extended periods of time was considered desirable.

However, after the first two hours, some problems were encountered with the humidity chamber whereby the humidity become erratic, dropping to 65% RH for the remainder of the test.

The results are given in the following Table.

TABLE 5

| | | CURL RETENTION | | | | | | | |
|---|---|---|---|---|---|---|---|---|---|
| | INITIAL | | | | (% Curl Retention) | | | | |
| RUN # | LENGTH** (cm) | 0.25 HR. | 0.5 HR. | 1.0 HR. | 1.5 HR. | 2 HRS. | 3 HRS.* | 4 HRS.* | 6 HRS.* | 24 HRS.* |
| 1 | 17.5 | 71.2 | 38.4 | 25.0 | 23.5 | 22.7 | 22.7 | 15.2 | 20.5 | 20.5 |
| 2 | 17.5 | 54.2 | 36.5 | 24.0 | 22.9 | 22.9 | 22.9 | 22.9 | 22.9 | 21.9 |
| 3 | 17.5 | 59.2 | 19.0 | 12.2 | 11.6 | 11.6 | 11.6 | 11.5 | 11.6 | 10.9 |
| 4 | 17.5 | 53.8 | 36.8 | 18.9 | 15.1 | 15.1 | 15.1 | 15.1 | 15.1 | 15.1 |
| 5 | 17.5 | 50.0 | 40.9 | 31.8 | 29.1 | 28.2 | 27.3 | 27.3 | 27.3 | 27.3 |
| 6 | 17.5 | 41.2 | 31.8 | 18.8 | 18.8 | 17.6 | 17.6 | 17.6 | 17.6 | 17.6 |
| AVG | | 54.9 | 33.6 | 21.8 | 20.2 | 19.7 | 18.3 | 18.3 | 19.2 | 18.9 |

* Relative humidity dropped from 90% to 65%
**Length of hair before curling

The curl retention of the tested polymer was excellent.

The above preferred embodiments and examples were given to illustrate the scope and spirit of the present invention. These embodiments and examples will make apparent to those skilled in the art other embodiments and examples. These other embodiments and examples are within the contemplation of the present invention. Therefore, the present invention should be limited only by the amended claims.

What is claimed is:

1. A hair conditioning composition comprising a cosmetic carrier and a hair conditioning effective amount of a homopolymer prepared from polymerizing a monomer of the formula:

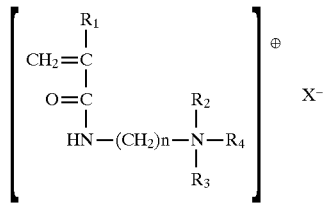

wherein $R_1$ is hydrogen or methyl;

$R_2$ and $R_3$ are independently lower alkyl;

$R_4$ is $C_1$–$C_{25}$ alkyl or aryl group;

n is 1–6; and

X is lower alkyl sulfate or aryl sulfonate.

2. The composition according to claim 1 wherein $R_2$ and $R_3$ are independently alkyl having 1–3 carbon atoms.

3. The composition according to claim 1 wherein $R_2$ and $R_3$ are the same.

4. The composition according to claim 1 wherein $R_2$ and $R_3$ are both methyl.

5. The composition according to claim 3 wherein $R_2$ and $R_3$ are both alkyl.

6. The composition according to claim 1 wherein $R_4$ is lower alkyl.

7. The composition according to claim 1 wherein $R_2$, $R_3$ and $R_4$ are independently lower alkyl.

8. The composition according to claim 1 wherein $R_2$, $R_4$ and $R_3$ are the same.

9. The composition according to claim 1 wherein X is $C_1$–$C_3$ alkyl sulfate or p-toluene sulfonate.

10. The composition according to claim 1 wherein X is $C_1$–$C_3$ alkyl sulfate or toluene sulfonate, and $R_2$, $R_3$ and $R_4$ are independently alkyl containing 1–3 carbon atoms.

11. The composition accordingly to claim 1 wherein the viscosity of the homopolymer ranges from about 7500 to about 100,000 cps.

12. The composition according to claim 1 wherein the homopolymer is present in amounts ranging from about 0.5 to about 5% by weight.

13. The composition according to claim 1 wherein an anionic, nonionic or amphoteric surfactant or mixtures thereof is additionally present.

14. The composition according to claim 1 wherein at least one of the group consisting of plasticizers, fragrances, dye, hair colorant, foam stabilizer, preservative, and a water softening agent is additionally present.

15. The composition according to claim 1 wherein the monomer is prepared by reacting DMAPMA with DMS.

16. The composition according to claim 1 wherein the monomer is prepared by reacting DMAPMA with DES or by reacting DMAPA with DMS.

17. The composition according to claim 1 wherein the carrier is water.

18. The composition according to claim 1 wherein the pH ranges from about 5 to about 7.5.

19. A hair conditioning composition comprising a cosmetic carrier, an anionic surfactant and a hair conditioning effective amount of a homopolymer prepared from polymerizing a monomer of the formula:

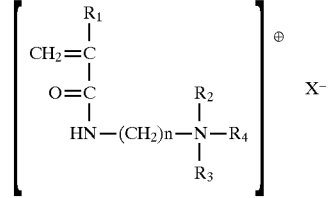

wherein $R_1$ is hydrogen or methyl;

$R_2$ and $R_3$ are independently lower alkyl;

$R_4$ is $C_1$–$C_{25}$ alkyl or aryl group;

n is 1–6; and

X is lower alkyl sulfate or aryl sulfonate.

20. The hair conditioning composition according to claim 19 wherein $R_2$ and $R_3$ are independently alkyl containing 1–3 carbon atoms and $R_4$ is lower alkyl.

21. The hair conditioning composition according to claim 19 wherein $R_4$ is lower alkyl.

22. The hair conditioning composition according to claim 19 wherein X is $C_1$–$C_3$ alkyl sulfate or p-toluene sulfonate.

23. The hair conditioning composition according to claim 19 wherein the cosmetic carrier is water and at least one of the group consisting of plasticizer, fragrance, dye, hair colorant, foam stabilizer, preservative and water softening agent is additionally present.

24. The hair conditioning composition according to claim 19 wherein X is $C_1$–$C_3$ alkyl sulfate or p-toluene sulfonate, and $R_2$, $R_3$ and $R_4$ are independently alkyl containing 1–3 carbon atoms.

25. The hair conditioning composition according to claim 19 wherein the homopolymer is the polymerization product of DMAPMA and DMS, or DMAPMA and DES or DMAPA and DMS.

26. A method of treating hair comprising contacting the hair for a sufficient time with a conditioning effective amount of the hair conditioning composition according to claim 1.

27. A method of imparting conditioning properties to hair comprising contacting hair for a time sufficient for the hair to interact with the hair conditioning composition of claim 1.

28. The method of claim 26 or 27 further comprising rinsing the hair with water after contacting the hair with the composition.

29. In a method of improving the solubility in water of a hair conditioning composition containing a cationic polymer in association with a cosmetic carrier, and optionally fragrance, dye, colorant, stabilizer, preservative, water softening agent, or shampoo containing a surfactant, the improvement comprising utilizing as the cationic polymer a homopolymer prepared from polymerizing a monomer of the formula:

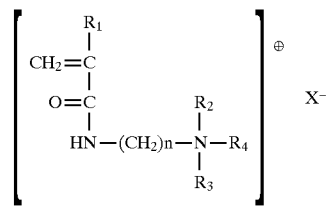

wherein $R_1$ is hydrogen or methyl;

$R_2$ and $R_3$ are independently lower alkyl;

$R_4$ is $C_1$–$C_{25}$ alkyl or aryl group;

n is 1–6; and

X is lower alkyl sulfate or aryl sulfonate.

30. A method of enhancing the hair sensitivity of a hair shampoo which comprises adding to said shampoo an effective amount of a homopolymer prepared from polymerizing a monomer of the formula:

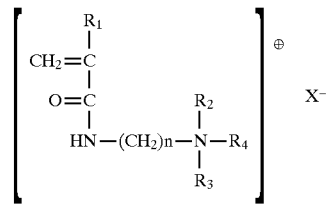

wherein $R_1$ is hydrogen or methyl;

$R_2$ and $R_3$ are independently lower alkyl;

$R_4$ is $C_1$–C25 alkyl or aryl group;

n is 1–6; and

X is lower alkyl sulfate or aryl sulfonate.

31. A method of conditioning tangled hair which comprises contacting said tangled hair with the hair conditioning composition of claim 1 for a time sufficient for the tangled hair to interact therewith.

* * * * *

UNITED STATES PATENT AND TRADEMARK OFFICE
CERTIFICATE OF CORRECTION

PATENT NO. : 5,863,526
DATED : January 26, 1999
INVENTOR(S) : Dominic Wai Kwing Yeung et al.

It is certified that error appears in the above-identified patent and that said Letters Patent is hereby corrected as shown below:

Column 13,
Line 16, Table 5, "38.4" should read -- 36.4 --

Column 15,
Line 1, "$C_{1\text{-}c25}$" should read -- $C_1$-$C_{25}$ --
Lines 28-31, "A method of imparting condition properties to hair comprising contacting hair for a time sufficient for the hair to interact with the air conditioning composition of Claim 1" should read -- A method of imparting conditioning properties to hair comprising contacting hair with a conditioning effective amount of hair conditioning of Claim 1 for a time sufficient for the hair to interact therewith. --.

Column 16,
Line 34, "$C_1$-C25" should read -- $C_1$-$C_{25}$ --

Signed and Sealed this

Sixteenth Day of December, 2003

JAMES E. ROGAN
*Director of the United States Patent and Trademark Office*